(12) United States Patent
Kuppusamy et al.

(10) Patent No.: US 8,722,707 B1
(45) Date of Patent: *May 13, 2014

(54) COMPOSITIONS AND METHODS FOR INHIBITION OF SMOOTH MUSCLE CELL PROLIFERATION AND NEOINTIMAL HYPERPLASIA

(75) Inventors: Periannan Kuppusamy, New Albany, OH (US); Kalman Hideg, Pécs (HU); Karuppaiyah Selvendiran, Columbus, OH (US)

(73) Assignee: The Ohio State University, Columbus, OH (US)

( * ) Notice: Subject to any disclaimer, the term of this patent is extended or adjusted under 35 U.S.C. 154(b) by 140 days.

This patent is subject to a terminal disclaimer.

(21) Appl. No.: 12/831,170

(22) Filed: Jul. 6, 2010

Related U.S. Application Data

(60) Provisional application No. 61/223,280, filed on Jul. 6, 2009.

(51) Int. Cl.
*A01N 43/40* (2006.01)
*A61K 31/44* (2006.01)

(52) U.S. Cl.
USPC ......................................................... 514/336

(58) Field of Classification Search
None
See application file for complete search history.

(56) References Cited

U.S. PATENT DOCUMENTS

| 2004/0176384 A1 | 9/2004 | Snyder et al. |
| 2007/0072912 A1 | 3/2007 | Hideg et al. |
| 2008/0280890 A1 | 11/2008 | Patil |

FOREIGN PATENT DOCUMENTS

WO  2011005790 A1  1/2011

OTHER PUBLICATIONS

PCT International Search Report and the Written Opinion, PCT/US10/41103 filed Jul. 6, 2010, dated Sep. 14, 2010.
Selvendiran, K. et al., "Inhibition of Vascular Smooth-Muscle Cell Proliferation and Arterial Restenosis by HO-3867, a Novel Synthetic Curcuminoid, through Up-Regulation of PTEN Expression," The Journal of Pharmacology and Experimental Therapeutics, 2009, vol. 329, No. 3, pp. 959-966.
Selvendiran, K. et al., "EF24 Induces G2/M Arrest and Apoptosis in Cisplatin-Resistant Human Ovarian Cancer Cells by Increasing PTEN Expression," Journal of Biological Chemistry, 2007, vol. 282, No. 39, pp. 28609-28618.

*Primary Examiner* — Leslie A. Royds Draper
(74) *Attorney, Agent, or Firm* — MacMillan, Sobanski & Todd, LLC

(57) ABSTRACT

Compositions and methods for treating post angioplasty restenosis, arteriosclerosis, and/or smooth muscle cell proliferation and/or neointimal hyperplasia in vascular tissues, and at least one composition of a redox based curcumin derivative, DAP-F(p) and a pharmaceutically acceptable carrier, are described.

8 Claims, 12 Drawing Sheets

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gccatcatca aagagatcgt                                              20

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggatcagagt cagtgg                                                  16

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtcaacggat ttggtcgtat t                                            21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agtcttctgg gtggcagtga t                                            21

US 8,722,707 B1

COMPOSITIONS AND METHODS FOR INHIBITION OF SMOOTH MUSCLE CELL PROLIFERATION AND NEOINTIMAL HYPERPLASIA

CROSS-REFERENCE TO RELATED APPLICATIONS

This application claims the benefit of U.S. Provisional Application Ser. No. 61/223,280 filed Jul. 6, 2009, the entire disclosure of which is expressly incorporated herein by reference.

STATEMENT REGARDING FEDERALLY SPONSORED RESEARCH

This invention was made with Government support and the Government has rights in this invention under the grant under the National Institutes of Health Grant No. CA102264 and Hungarian Research Fund Grant OTKA T048334.

TECHNICAL FIELD AND INDUSTRIAL APPLICABILITY OF THE INVENTION

The present invention relates to compositions and methods for treating post angioplasty restenosis, arteriosclerosis, and/or smooth muscle cell proliferation and/or neointimal hyperplasia in vascular tissues.

SEQUENCE LISTING

The instant application contains a Sequence Listing which has been submitted via EFS-web and is hereby incorporated by reference in its entirety. The ASCII copy, created on Mar. 2, 2011, is named 604_50914_SEQ_LIST_OSU-08058.txt, and is 1,291 bytes in size.

BACKGROUND OF THE INVENTION

Restenosis after angioplasty procedures or intracoronary stenting is a significant clinical problem. A dominant cellular event in the re-narrowing of the vascular lumen after angioplasty is smooth muscle cell (SMC) proliferation and migration. After vascular injury, the SMCs start to proliferate and then migrate into the developing neointima, thus becoming the major cellular substrate of the restenotic tissue. The rough-surfaced endoplasmic reticulum in SMCs can express a large number of growth-regulatory molecules and extracellular matrix (ECM) components.

SMC migration is regulated by insulin-like growth factor-1 (ILGF-1), platelet derived growth factor (PDGF), basic fibroblast growth factor (bFGF), as well as several other signaling factors. However, the precise molecular mechanisms that regulate SMC migration are not fully understood.

Numerous drugs have been tested for their ability to prevent restenosis. However, most have failed to reduce the incidence of restenosis appreciably. The control of SMC proliferation by activation of tumor suppressor genes such as p53, PTEN (phosphatase and tensin homolog mutated in multiple advanced cancers), and blocking the genes involved in cell-cycle progression was a recent development with potentially relevant clinical applications. For example, PTEN has been reported to regulate cardiac myocyte hypertrophy and survival as well as many of the angiogenic responses of vascular endothelial cells. A recent report also show that overexpression of PTEN could inhibit growth factor-induced proliferation, migration, and survival of vascular smooth muscle cells. The inhibitory effect of PTEN on neointimal formation was demonstrated in a rat carotid arterial balloon injury model and in aorteriocoronary saphenous vein grafts. However, the role of PTEN in molecular-signaling mechanisms, such as cell-cycle modulation, has not yet been elucidated.

It would be useful to have effective methods of treating and/or preventing the factors that cause restenosis, arteriosclerosis, and/or neointimal hyperplasia.

SUMMARY OF THE INVENTION

In a broad aspect, there is provided herein a method for inhibiting human aortic smooth muscle cell (SMC) proliferation in a subject in need thereof.

Other compositions, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

FIG. 1A: Effect of HO-3867 on the survival of serum (FBS)-stimulated SMCs. *, $p<0.05$ versus untreated cells.

FIG. 1B: Phase-contrast microscopy images (100×) of SMCs incubated with vehicle only (Control) or with 10 µM HO-3867 for 24 h.

FIG. 1C: Fluorescence microscopy images (200×) of DAPI-stained (blue) SMCs treated with vehicle (Control) or with 10 µM HO-3867 for 24 h.

FIG. D: Representative (of n=6) flow cytometric data showing cell cycle (DNA content) distribution in SMCs incubated with vehicle or with 10 µM HO-386 for 12 or 24 h.

FIG. E: Cell cycle (DNA content) distribution (percentage of total) in the treatment groups shown in FIG. 1D. Data represent mean±S.E.M. (n=6). *, $p<0.05$ versus control.

Figure 2A:
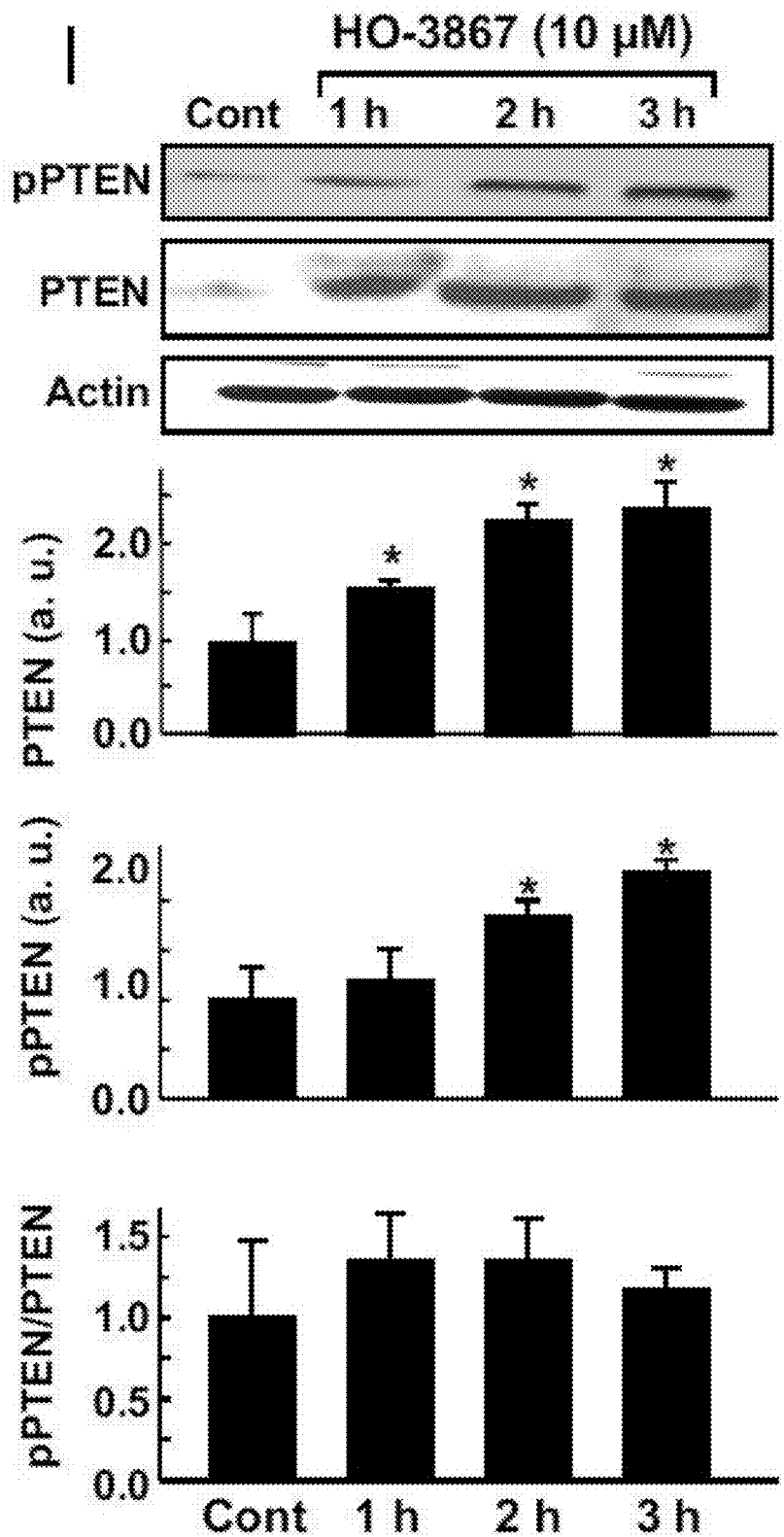
Figure 2B:
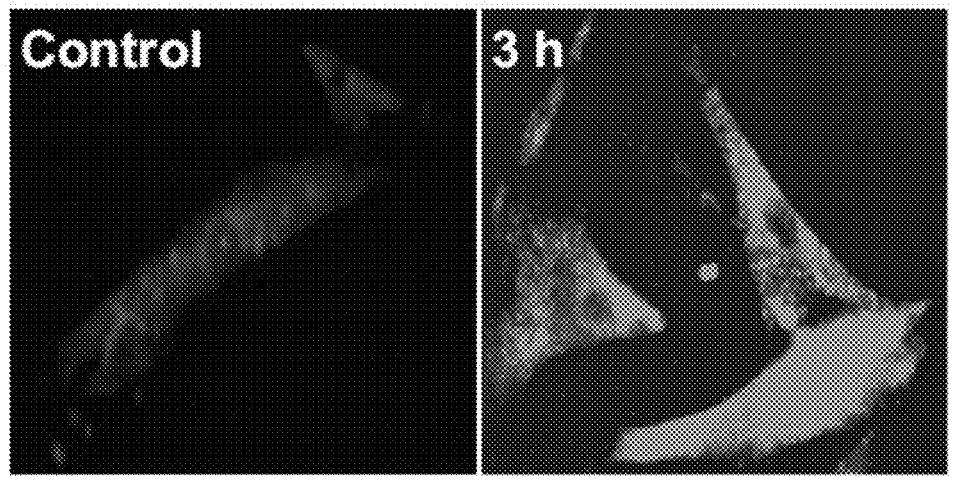
Figure 2C:
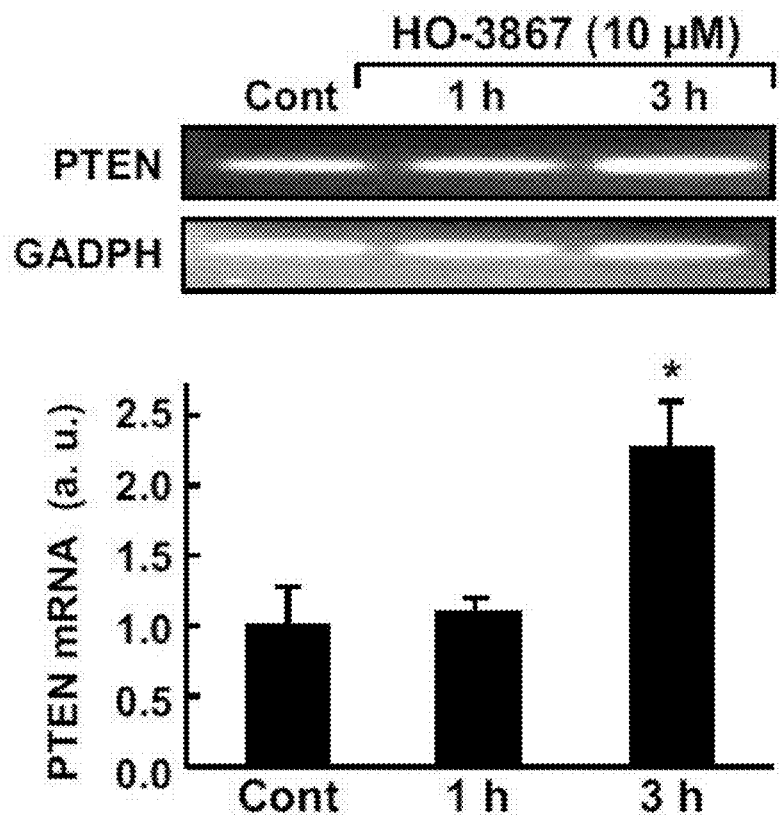

FIGS. 2A-2C: HO-3867 up-regulates PTEN expression in human SMCs.

FIG. 2A: Immunoblots of phosphorylated PTEN (pPTEN) and total PTEN expressions in SMCs treated with HO-3867 for 1, 2, or 3 h. Also shown are quantitative results of densitometry analysis of bands and pPTEN/PTEN ratio. Data represent the mean±S.E.M. (n=6). *, $p<0.05$ versus control.

FIG. 2B: Immunofluorescence images (400×, obtained using Alexa Fluor 488-conjugated anti-PTEN antibody) of PTEN expression in SMCs treated with 10 mM HO-3867.

FIG. 2C: RT-PCR analysis of PTEN mRNA expression in SMCs treated with 10 mM HO-3867. *, $p<0.05$ versus control.

Figure 3A:
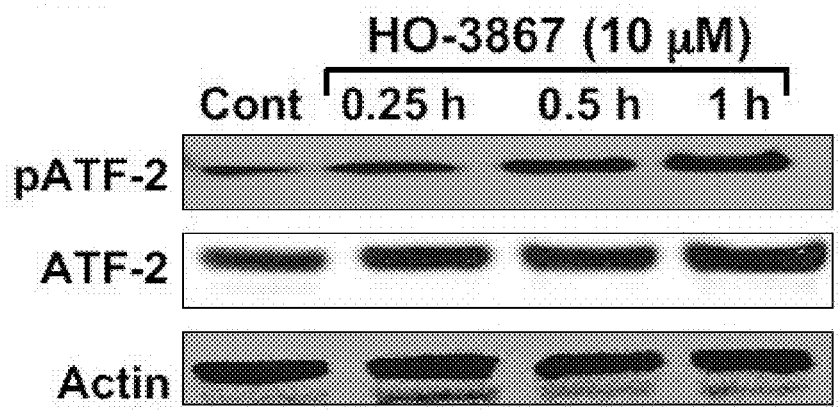
Figure 3B:
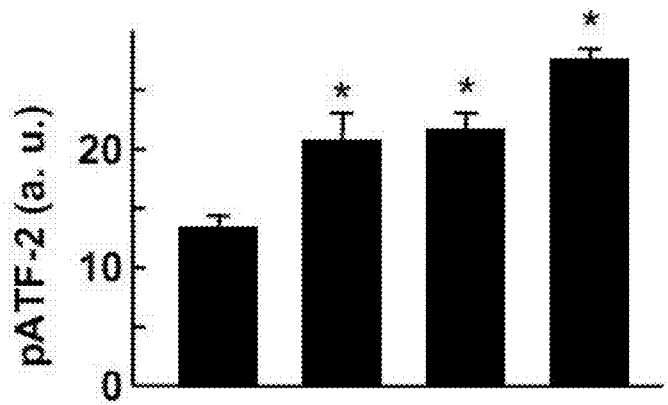
Figure 3C:
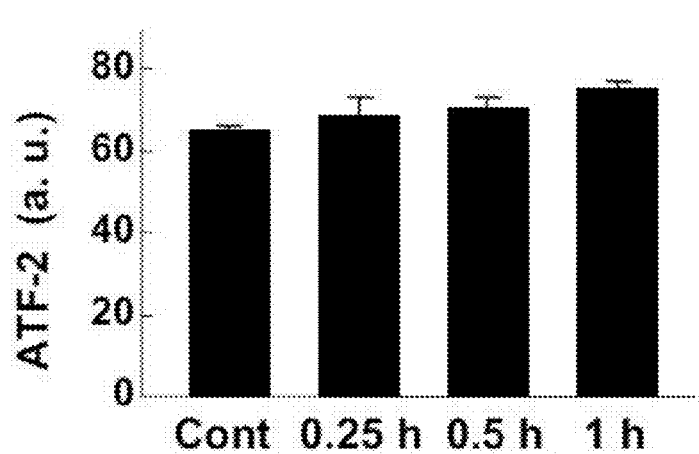

FIGS. 3A-3C: HO-3867 up-regulates ATF-2 activation in human SMCs.

FIG. 3A: Immunoblots of pATF-2 and total ATF-2 expressions in SMCs treated with 10 mM HO-3867. Also shown are quantitative results of densitometry analysis of pATF-2 (FIG. 3B) and ATF-2 (FIG. 3C) bands. Data represent the mean±S.E.M. (n=6).

FIGS. 4A-4D: PTEN siRNA inhibits HO-3867-induced cell cycle arrest.

Figure 4A:
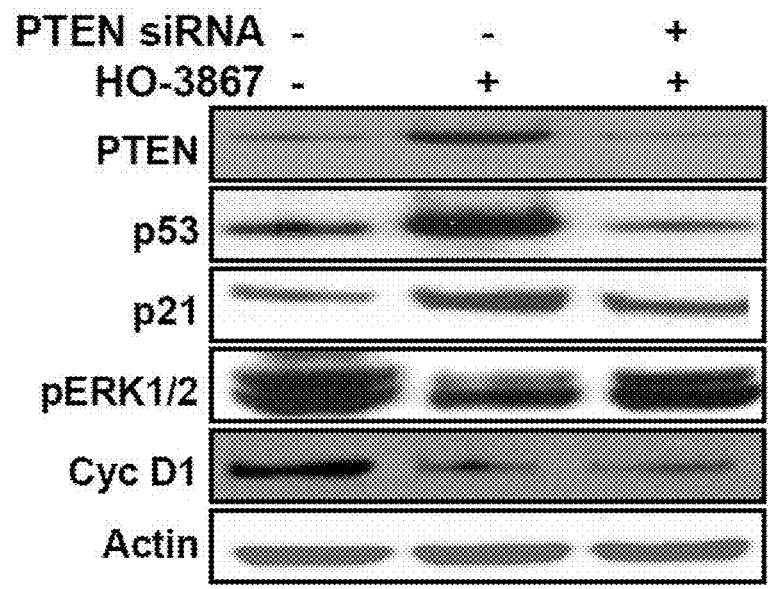

FIG. 4A: Effect of PTEN siRNA on HO-3867-induced up-regulation of PTEN expression. Representative Western blot images from PTEN siRNA-transfected SMCs treated with 10 μM HO-3867 for 24 h are shown.

Figure 4B:
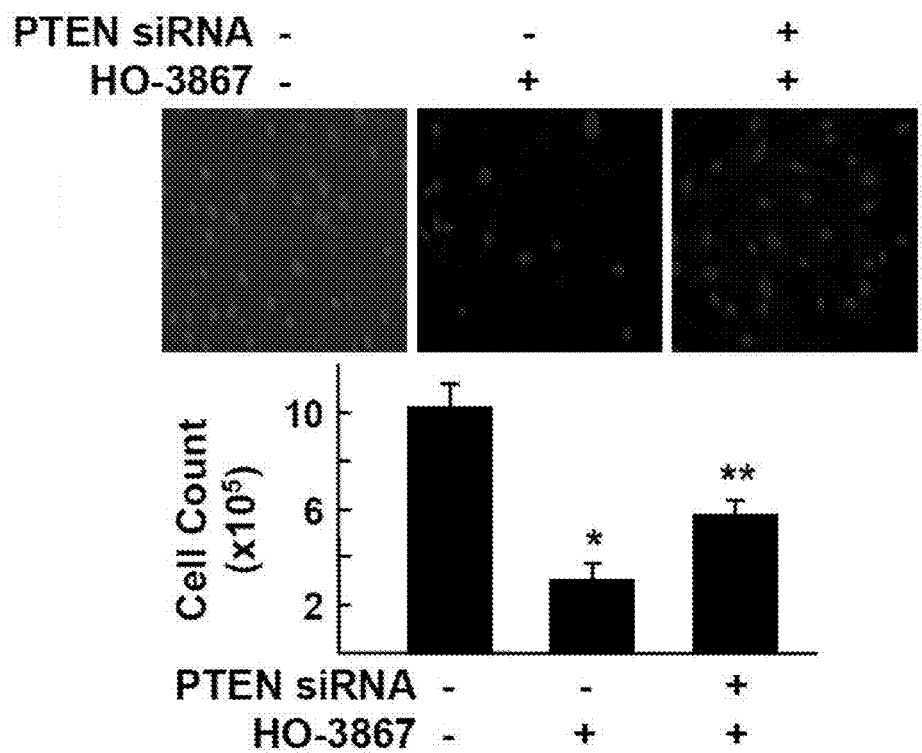

FIG. 4B: Fluorescence microscopy images (200×) of DAPI-stained (blue) PTEN siRNA-transfected SMCs treated with 10 μM HO-3867 for 24 h. Bar graph, cell count; expressed as mean±S.E.M. (n=3). *, p<0.05 versus control (−/−); **, p<0.05 versus HO-3867 group (−/+).

Figure 4C:
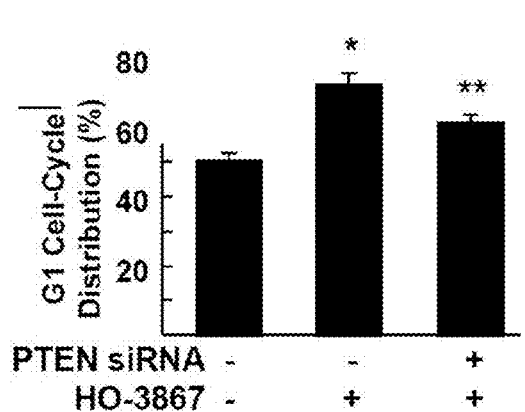

FIG. 4C: $G_1$ cell cycle (DNA content) distribution (percentage of total) in PTEN siRNA-transfected SMCs treated with 10 μM HO-3867 for 24 h. Data represent mean±S.E.M. (n=6). *, p<0.05 versus control (−/−); **, p<0.05 versus HO-3867 group (−/+).

Figure 4D:
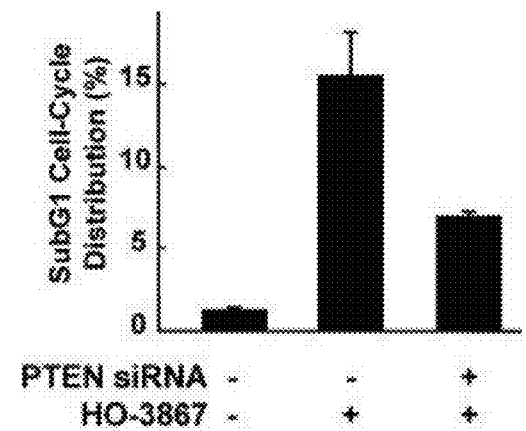

FIG. 4D: Quantification of sub-$G_1$ cell cycle population by flow cytometry in PTEN siRNA-transfected cells treated with 10 μM HO-3867 for 48 h.

Figure 5A:
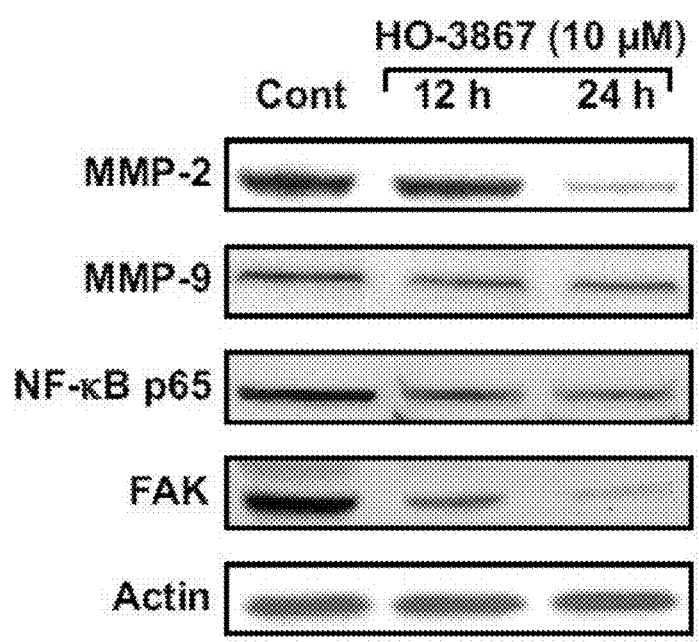
Figure 5B:
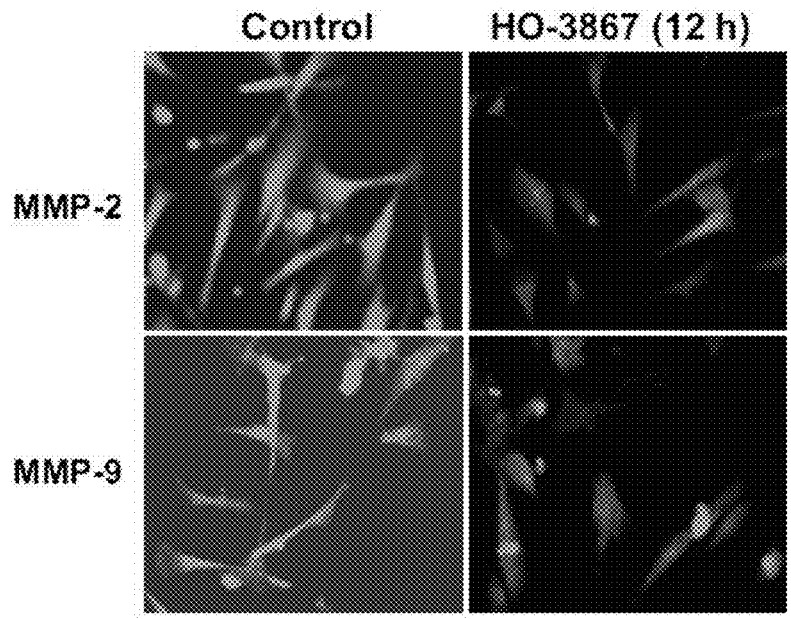

FIGS. 5A-5B: HO-3867 down-regulates MMP-2, MMP-9, NF-κB, and FAK expression. SMCs were treated with 10 μM HO-3867 for 12 or 24 h.

FIG. 5A: Western blot images showing down-regulation of SMC proliferation genes MMP-2, MMP-9, NF-κB, and FAK after 24-h exposure.

FIG. 5B: Immunofluorescence images of MMP-2 and MMP-9 expression (100×) at 12-h treatment.

FIGS. 6A-6D: PTEN overexpression induces apoptosis in SMCs. The PTEN/FLAG gene was transfected into SMCs, which were then treated with 10 μM HO-3867 for 12 or 24 h.

Figures 6A, 6B:
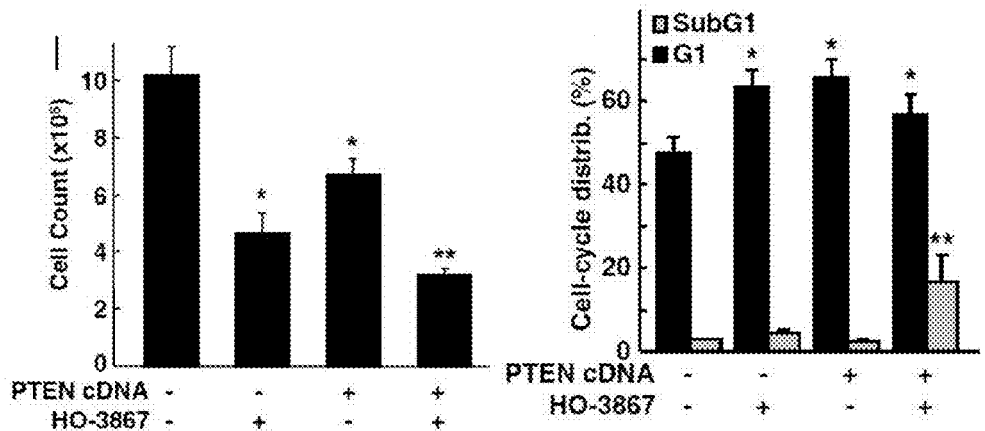

FIG. 6A: Effect of PTEN overexpression on HO-3867-induced inhibition of cell survival after 24 h.

FIG. 6B: Cell cycle distribution in PTEN cDNA-transfected cells treated with HO-3867 for 12 h. Data represent mean±S.E.M. (n=6). *, p<0.05 versus untreated control cells; **, p<0.05 versus PTEN cDNA (+/−) or HO-3867 (−/+) group. Combination of PTEN cDNA and HO-3867 exposure had a significantly greater effect compared with the HO-3867- or cDNA alone-treated groups. Data represent mean±S.E.M. (n=6). *, p<0.05 versus control group (−/−); **, p<0.05 versus PTEN cDNA group ((+/−).

Figure 6C:
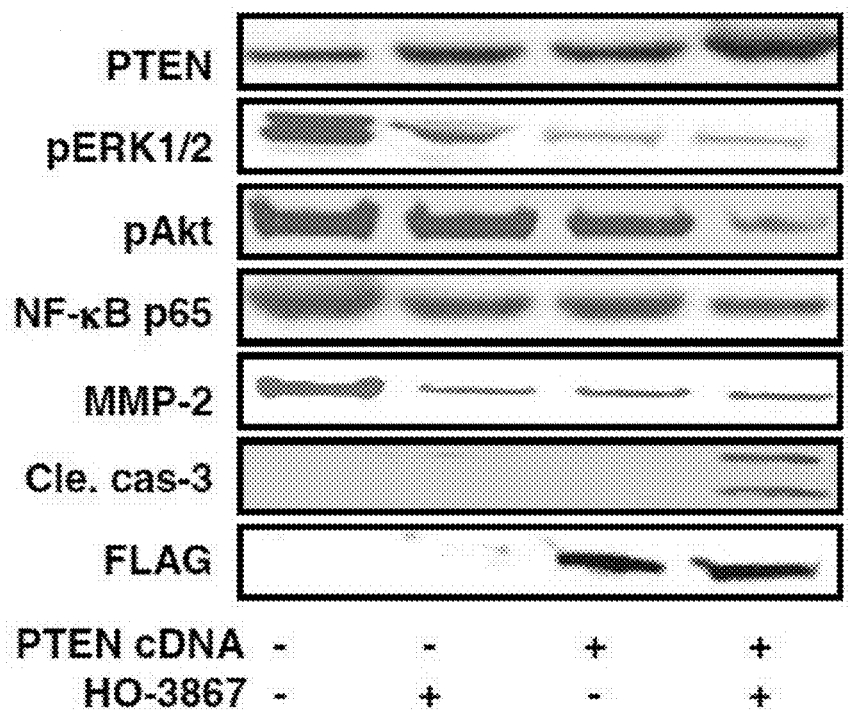

FIG. 6C: Western blot images showing the effect of PTEN overexpression and 10 μM HO-3867 treatment (12 h) on pERK1/2, NF-κB, MMP-2, and MMP-9 protein levels.

Figure 6D:
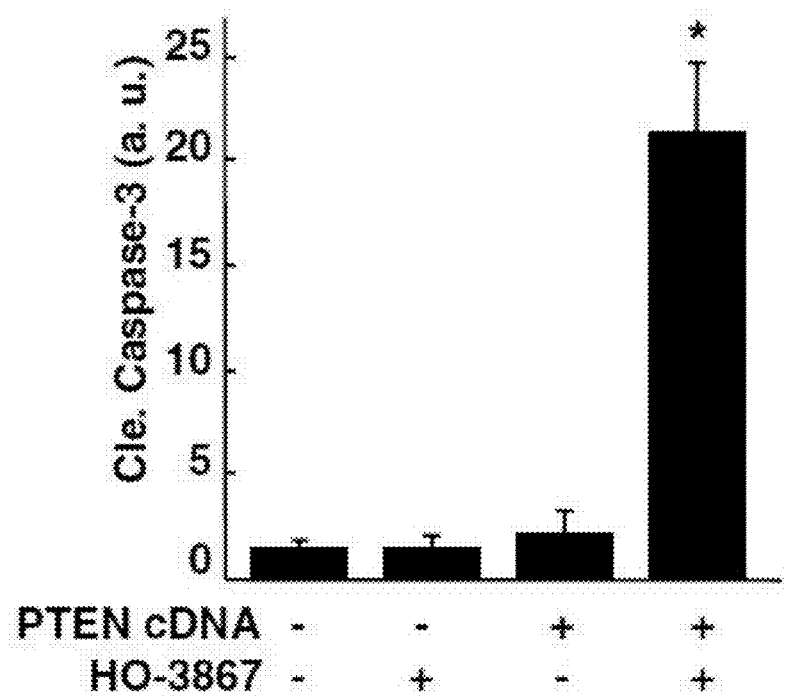

FIG. 6D: Cleaved caspase-3 levels showing substantial increase in the combination treatment (+/+) group. Data represent mean±S.E.M. (n=6). *, p<0.05 versus PTEN cDNA (+/−) or HO-3867 (−/+) group.

FIGS. 7A-7E: HO-3867 inhibits neointima formation and up-regulates PTEN expression after rat carotid artery injury.

Figure 7A:
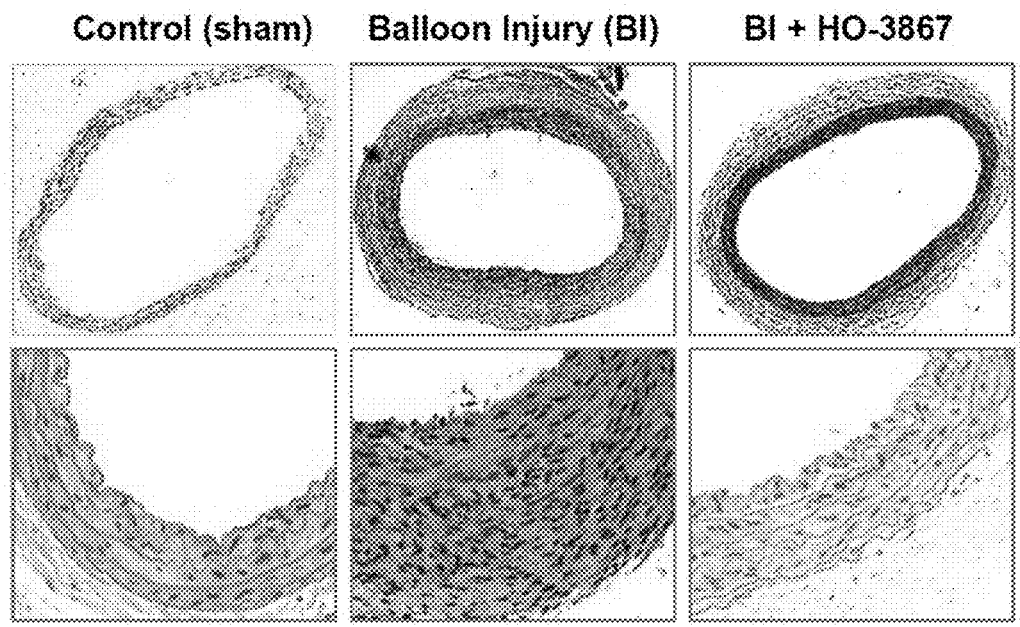

FIG. 7A: Representative cross-sections of uninjured (Control) and injured carotid arteries with (HO-3867) and without [balloon injury (BI)] HO-3867 treatment at 10 mg/kg. The cross sections were magnified and photographed at 10× and 40×. Cell proliferation is observed in both injured and treatment groups.

Figure 7B:
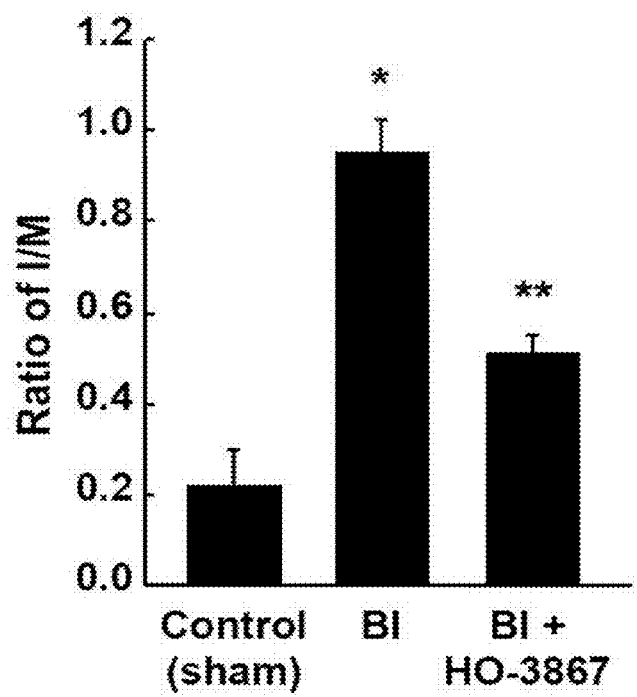

FIG. 7B: Morphometric measurements of neointima formation in uninjured or injured carotid arteries at 2 weeks after treatment. Data represent mean±S.E.M. (n=5). *, p<0.05 versus control; **, p<0.05 versus injured/untreated (BI).

Figure 7C:
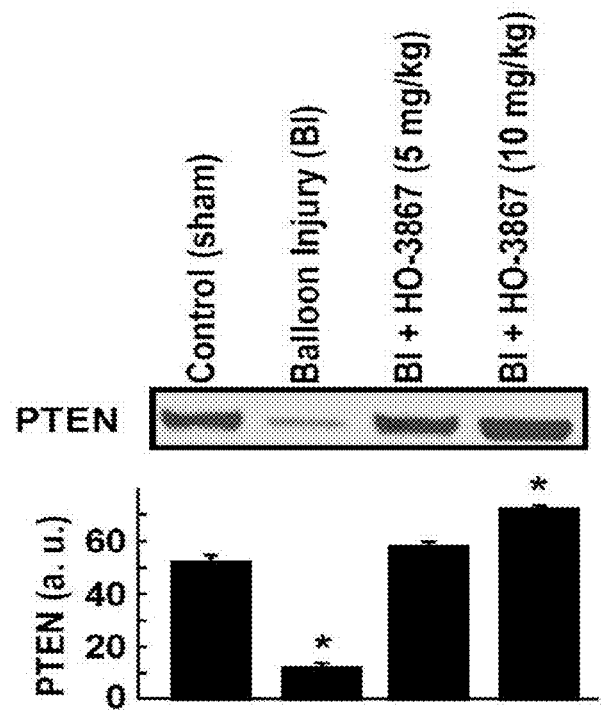

FIG. 7C: PTEN expression was drastically decreased in the BI group compared with the uninjured control group. HO-3867 treatment rescued PTEN levels in the group treated with 10 mg/kg. Densitometry analyses of visualized bands were performed for quantitation of PTEN expression. The data represent mean±S.E.M. (n-3). *, p>0.05 versus control.

Figure 7D:
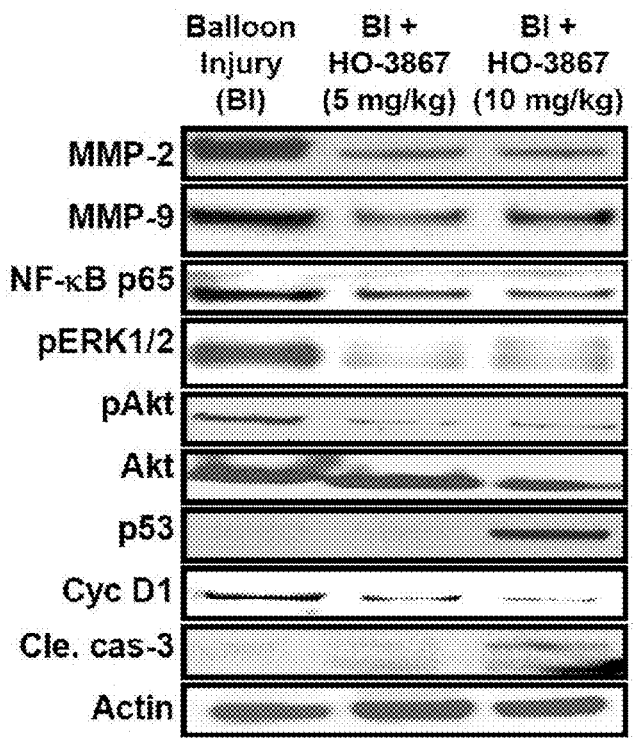

FIG. 7D: Protein expression of MMP-2, MMP-9, NF-κB, FAK, pERK1/2, pAkt, and cyclin D1 as analyzed by Western blotting.

Figure 7E:
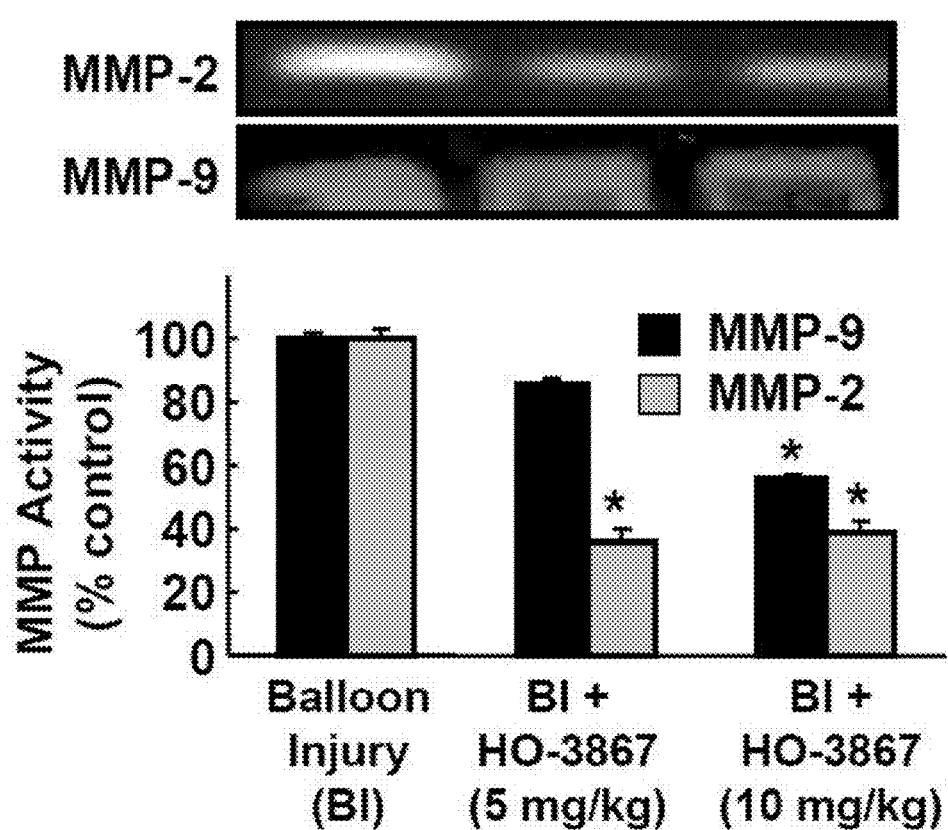

FIG. 7E: MMP-2 and MMP-9 activity. Data represent mean±S.E.M. (n=5). *, p<0.05 versus untreated control.

DETAILED DESCRIPTION OF THE PREFERRED EMBODIMENT

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the subject invention provides methods and compositions altering the amount of a target genome in a target cell. In further describing the subject invention, the subject methods are described first in greater detail, followed by a review of various representative applications in which the subject invention finds use as well as kits that find use in practicing the subject invention Introduction There is provided herein compositions comprising a redox based curcumin derivative. In particular, the composition comprising a redox based curcumin derivative, diarylidenylpiperiden-4-one (DAP) having a hydroxylamine moiety attached thereto, and generally having the structure:

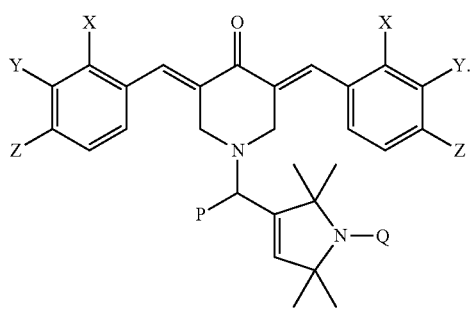

Formula I

X, Y, Z = H, F, CF, or any combination thereof
Q = H, OH, or O
P = H₂, or O

In certain embodiments, the composition has the general structure:

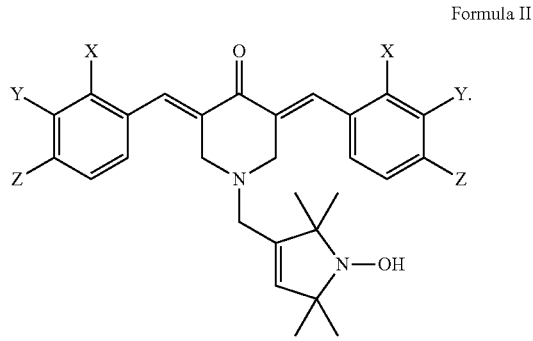

Formula II

X = F, Y = H, Z = H: DAP-F(o)-NOH
X = H, Y = F, Z = H: DAP-F(m)-NOH
X = H, Y = H, Z = F: DAP-F(p)-NOH
X = F, Y = F, Z = H: DAP-F₂(o,m)-NOH
X = F, Y = H, Z = F: DAP-F₂(o,p)-NOH
X = H, Y = F, Z = F: DAP-F₂(m,p)-NOH

For example, one useful composition is DAP-F(p)-NOH (1-[(1-oxyl-2,2,5,5-tetramethyl-2,5-dihydro-1H-pyrrol-3-yl)methyl]-(3E,5E)-3,5-bis(4-fluorobenzylidene) piperidin-4-one)[HO-3867] having the structure:

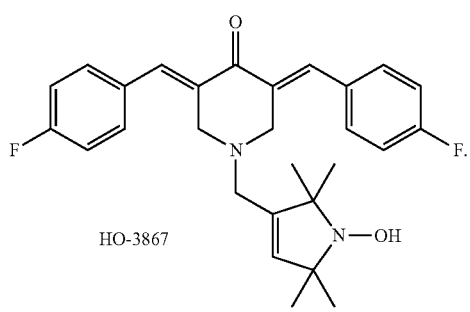

Formula III

HO-3867

The compositions of Formulae I-III are useful for providing protection to normal cells from associated oxidative damage, while simultaneously providing a desired treatment of post angioplasty restenosis, arteriosclerosis, and/or smooth muscle cell proliferation and/or neointimal hyperplasia.

The compositions have in vivo cleavable hydroxylamine formed on an available pyridine group. The compositions are capable of undergoing redox cycling to its correspondent nitroxide form in vivo. Also, the compositions are capable of inducing the generation of reactive oxygen species (ROS) in certain cells, yet not significantly inducing the generation of ROS in normal cells. As such, the compositions are useful to provide protection to normal cells from associated oxidative damage, while simultaneously providing a desired therapeutic efficacy. These compositions are thus useful in treating acute or chronic free-radical associated diseases.

The composition include a covalent coupling of a hydroxylamine moiety to a DAP-F(p) composition. That is, the compositions can be considered a bifunctional composition having a diarylidenyl piperidone (DAP) moiety conjugated to a nitroxide precursor (NOH) moiety, where the DAP moiety has cytotoxic activity, and the NOH moiety functions as a tissue-specific modulator of cytotoxicity.

The composition are useful for the treatment of post angioplasty restenosis, arteriosclerosis, and/or smooth muscle cell proliferation and/or neointimal hyperplasia in vascular tissues.

In certain embodiments, the compositions are useful for the treatment of human aortic smooth muscle cell (SMC) proliferation in a subject in need thereof.

Also, in certain embodiments, the compositions are useful for increasing PTEN expression and activity in SMCs in a subject in need thereof.

The composition can also be used for downregulating one or more of: MMP-2, MMP-9, NF-κB and FAK in a subject in need thereof.

Further, the composition can be used for inducing overexpression of PTEN by PTEN cDNA in order to enhance apoptosis in smooth muscle cells (SMCs) arrest in a subject in need thereof.

In still other embodiments, the composition are useful for inhibiting neointimal formation after injury in an artery in a subject in need thereof.

In still other embodiments, the compositions are useful for inhibiting FBS-induced SMC proliferation through cell-cycle arrest at the G1 phase, as well as by induction of apoptosis in a subject in need thereof.

In still other embodiments, the compositions are useful for activating PTEN and one or more growth-regulatory proteins including cyclin D1, MMPs, NF-κB, and ERK1/2 in a subject in need thereof.

In still other embodiments, the compositions are useful for reducing intimal thickening of a blood vessel wall in a subject in need thereof.

Also described herein are methods for providing protection to normal cells from associated oxidative damage, while simultaneously providing a desired therapeutic efficacy.

The present invention is based, at least in part, on the inventors' discovery that the novel synthetic composition, HO-3867, is useful for the inhibition of SMC proliferation.

The inventors have now determined that the pharmacologic inhibition of human aortic SMC proliferation in vitro and a substantial reduction in neointimal formation in vivo is achieved by the administration of HO-3867. Also, the HO-3867 inhibited FBS-induced SMC proliferation through cell-cycle arrest at the G1 phase, as well as by induction of apoptosis. While the inventors do not intend to be bound by theory, the following is a description of the basis for the invention.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified. The value of the present invention can thus be seen by reference to the Examples herein.

Example 1

Material and Methods

Reagents.
Dimethyl sulfoxide (DMSO) and antibodies directed against actin and FLAG were obtained from Sigma-Aldrich (St. Louis, Mo.). Clonetics smooth muscle cell basal medium, fetal bovine serum, antibiotics, sodium pyruvate, trypsin, and phosphate-buffered saline (PBS) were obtained from Invitrogen (Carlsbad, Calif.). Polyvinylidene fluoride membrane and molecular weight markers were obtained from Bio-Rad (Hercules, Calif.). Antibodies directed against Akt, pAkt (Ser473), ERK1/2, phosphorylated (p) ERK1/2, PTEN, pPTEN (Ser38 0 and Thr38 1/38 2), NF-κB, cleaved caspase-3, and PTEN siRNA kit were purchased from Cell Signaling Technology Inc. (Danvers, Mass.). PTEN plasmid (plasmid 1078 6; 1437 pSG 5L Flag HAPTEN) was obtained from Addgene Inc. (Cambridge, Mass.). Antibodies directed against cyclin D1, p53, p21, p27, matrix metalloproteinase (MMP)-2, MMP-9, and focal adhesion kinase (FAK) were obtained from Santa Cruz Biotechnology, Inc. (Santa Cruz, Calif.). RNase was obtained from Promega (Madison, Wis.). Enhanced chemiluminescence reagents were obtained from G E Healthcare (Chalfont St. Giles, Buckinghamshire, UK).

A composition labeled herein as HO-3867 and having the structure set forth below was synthesized

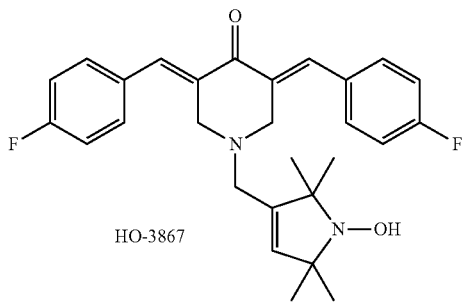 [SMILES: CC1(C)C=C(CN2C/C(=C\c3ccc(F)cc3)C(=O)/C(=C/c3ccc(F)cc3)C2)C(C)(C)N1O]

HO-3867

Synthesis of HO-3867

Melting points were determined with a Boetius micromelting point apparatus and are uncorrected. Elemental analyses (C, H, N, S) were done on a Fisons EA 1110 CHNS elemental analyzer. Mass spectra were recorded on Thermoquest Automass Multi and VG TRIO-2 instruments the EI mode. $^1$H NMR spectra were recorded with a Varian UNITYINOVA 400 WB spectrometer. Chemical shifts are referenced to Me4Si. Measurements were run at 298K probe temperature in a CDCl$_3$ solution. Flash column chromatography was done on a Merck Kieselgel 60 (0.040-0.063 mm). Qualitative thin-layer chromatography was carried out on commercially prepared plates (20×20×0.02 cm) coated with Merck Kieselgel GF254. All chemicals were purchased from Aldrich.

1-[(1-Oxyl-2,2,5,5-tetramethyl-2,5-dihydro-1H-pyrrol-3-yl)methyl]-(3E,5E)-3,5-Bis(4-fluorobenzylidene)piperidin-4-one (HO-3867)

A mixture of H-4073 HCl salt (1.73 g, 5.0 mmol) and K2CO3 (1.38 g, 10.0 mmol) in acetonitrile (20 mL) was stirred at room temperature for 30 minutes. Then, allylic bromide and HO-350 (1.28 g, 5.5 mmol) were added dissolved in acetonitrile (5 mL) and the mixture was stirred and refluxed till the consumption of the starting materials (~3 h). After cooling, the inorganic salts were filtered off on sintered glass filter, washed with CHCl3 (10 mL), the filtrate was evaporated, and the residue was partitioned between CHCl$_3$ (20 mL) and water (10 mL). The organic phase was separated; the aqueous phase was washed with CHCl$_3$ (20 mL); and the combined organic phase was dried (MgSO$_4$), filtered, and evaporated. The residue was purified by flash column chromatography (Hexane/EtOAc) to obtain the deep yellow solid title composition [1.36 g (59%), R$_f$: 0.57 (Hexane/EtOAc, 2:1), mp 142-144° C. MS (EI, 70 eV): m/z (%): 463 (M+, 12) 433 (20), 324 (40), 310 (43), 133 (100). Electron spin resonance: a$_N$=14.9 G. Anal Calcd. for: C$_{28}$H$_{29}$F$_2$N$_2$O$_2$: C, 72.55; H, 6.31; N, 6.04. Found: C, 72.54; H, 6.23; N, 6.04].

To achieve the N-hydroxy composition HCl salt, HO-3867 (1.0 g) was dissolved in ethanol (20 mL, saturated with HCl gas previously) and refluxed for 30 minutes. Then, the solvent was evaporated off and the procedure was repeated till the disappearance of the electron paramagnetic resonance triplet line to give the HCl salt. Stock solutions of the compositions were freshly prepared in DMSO. HO-3867 was prepared in 0.5% DMSO for in vitro studies.

Cell Culture.
Human aortic SMCs were obtained at passage 3 (AoSMC; Lonza Walkersville, Inc., Walkersville, Md.). The cells were maintained in culture in a humidified incubator at 37 C and 5% CO2 in smooth muscle cell growth medium (SmG M-2). Cells were trypsinized and passaged at 95% confluence. Studies were performed using cells at passages 4 to 6 at 6 0 to 90% confluence. Cells were counted using an automated cell counter (NucleoCounter; New Brunswick Scientific, Edison, N.J.).

Cell Cycle Analysis.
Flow cytometry was performed (Selvendiran K, Bratasz A, Tong L, Ignarro L J, and Kuppusamy P, NCX-4016, a nitro-derivative of aspirin, inhibits EGFR and STAT3 signaling and modulates Bcl-2 proteins in cisplatin-resistant human ovarian cancer cells and xenografts. Cell Cycle 7 :8188).

Western Blotting.
Western blotting was performed as reported previously (Selvendiran K, Tong L, Vishwanath S, Bratasz A, Trigg N J, Kutala V K, Hideg K, and Kuppusamy P, EF 24 induces G 2/M arrest and apoptosis in cisplatin-resistant human ovarian cancer cells by increasing PTEN expression. J Biol Chem 282::28609-28618).

Gelatin Zymography.
MMP-2 and MMP-9 was determined by gelatin zymography as reported previously (Cho and Reidy, 2002). Matrix metalloproteinase-9 is necessary for the regulation of smooth muscle cell replication and migration after arterial injury. Circ Res 91:845-851).

Immunofluorescence.

SMCs, grown on Lab-Tek Chamber slides (Nalge Nunc International, Rochester, N.Y.), were fixed with 4% paraformaldehyde for 10 min at room temperature and then washed in PBS containing 0.05% Tween 20. Nonspecific reactions were blocked with Protein B lock Serum-Free (DAKO, Kyoto, Japan) and then incubated with an anti-PTEN, MMP-2, or MMP-9 antibody at 4 C overnight. After washing in PBS containing 0.05% Tween 20, the specimens were treated with Alexa Fluor goat anti-mouse IgG (H+L) antibody (Invitrogen, Carlsbad, Calif.) for 45 min at room temperature and then counterstained by propidium iodide after digestion of RNA by RNase (Invitrogen). The immunostaining of PTEN, MMP-2, and MMP-9 proteins was visualized using a fluorescence microscope (Nikon, Tokyo, Japan).

PTEN siRNA and PTEN cDNA Transfection.

The PTEN siRNA and cDNA transfection experiments were performed as reported (Selvendiran et al., 2007, supra).

Reverse Transcription-PCR.

Total RNA was isolated from SMCs using the RNeasy system according to the instructions of the manufacturer. RNA quantification was done using spectrophotometry. Reverse transcription (RT)-PCR analysis for the mRNA expressions in PTEN and the internal control GAPDH was carried out using a GeneAmp PCR System Veriti thermo cycler (Applied Biosystems, Foster City, Calif.) under the following conditions: initial denaturation at 94 C for 2 min, 35 cycles of amplification (denaturation at 94 C for 30 s, annealing at 50 C for 30 s, and extension at 72 C for 30 s), and extension at 72 C for 5 min. The sequences (5'-3') for the primer pairs of PTEN and GAPDH, respectively, were as follows:

PTEN, GCCATCATCAAAGAGATCGT (forward) [SEQ ID NO:1], and

GGATCAGAGTCAGTGG (reverse) [SEQ ID NO:2];

and GAPDH, GTCAACGGATTTGGTCG-TATT (forward) [SEQ ID NO:3], and AGTCTTCTGGGTGGCAGT-GAT (reverse) [SEQ ID NO:4].

The PCR products were electrophoresed on 1.5% agarose gel and stained with ethidium bromide.

Carotid Artery Balloon Injury.

All experiments involving animals were performed in accordance with the relevant guidelines and regulations approved by the Internal Animal Care and Use Committee of The Ohio State University. Sprague-Dawley rats weighing 300 to 350 g were anesthetized by an intraperitoneal injection of ketamine (6 0 mg/kg) and xylazine (5 mg/kg). Under a stereomicroscope, the right common, external, and internal carotid arteries were exposed by a longitudinal midline cervical incision. Blood flow was temporarily interrupted by ligation of the common and internal carotid arteries using vessel clips. The external carotid artery was ligated permanently using 6-0 silk suture. A 2F Fogarty arterial embolectomy catheter (Edwards Lifesciences, Irvine, Calif.) was introduced through an arteriotomy in the external carotid artery just below the ligature and advanced to the common carotid artery. To produce the injury, the balloon was inflated with saline and passed six times with rotation from just under the proximal edge of the omohyoid muscle to the carotid bifurcation. The balloon was then deflated, and the catheter was withdrawn. Blood flow was restored by removing the clips on the common and internal carotid arteries. After visual inspection to ascertain adequate pulsation of the common carotid artery, the surgical incision was closed, and the rats were allowed to recover from anesthesia in a humidified and warmed chamber for 2 to 4 h.

Immediately after completion of the carotid injury procedure, subcutaneous administration of HO-3867 (in 10% DMSO+40% polyethylene glycol+50% PBS) commenced at a dose of 5 or 10 mg/kg/day, and continued for 2 weeks (n=5 for each group). The control group received the vehicle only. After treatment for 14 days, the animals were sacrificed with an overdose of pentobarbital (200 mg/kg), and the carotid arteries were collected for morphometric analysis and isolation of proteins for analysis by Western blotting. For morphometric analysis, carotid arteries were fixed in 10% formalin, dehydrated, and embedded in paraffin. Sections of 5-μm thickness were obtained at equally spaced intervals in the middle of the injured (experimental) and uninjured (control) common carotid artery segments. The samples were stained with hematoxylin and eosin. The intimal and medial areas were measured using MetaMorph software (Molecular Devices, Sunnyvale, Calif.), and intimal/medial ratios were calculated.

Statistical Analysis.

Data were expressed as mean±S.E.M. Comparisons among groups were performed using a Students t test. The significance level was set at $p<0.05$.

Results

HO-3867 Inhibits Human Aortic SMC Proliferation through $G_1$ Cell Cycle Arrest.

Figure 1A:
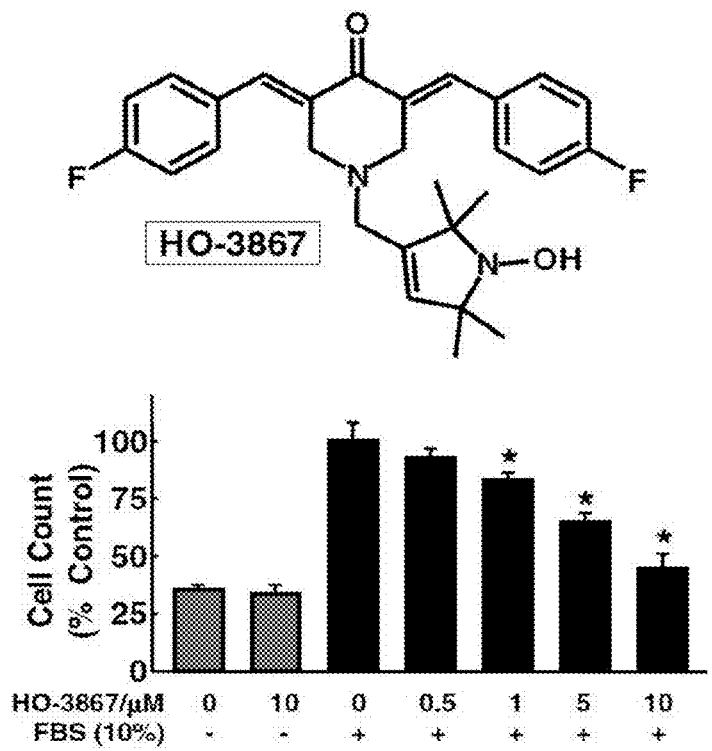
FIGS. 1A-1E: Effect of HO-3867 on cell survival, cell cycle arrest, and apoptosis in human aortic SMCs.

We first studied the effect of HO-3867 on serum-stimulated proliferation of human aortic SMCs, in vitro (FIG. 1A).

Figure 1B:
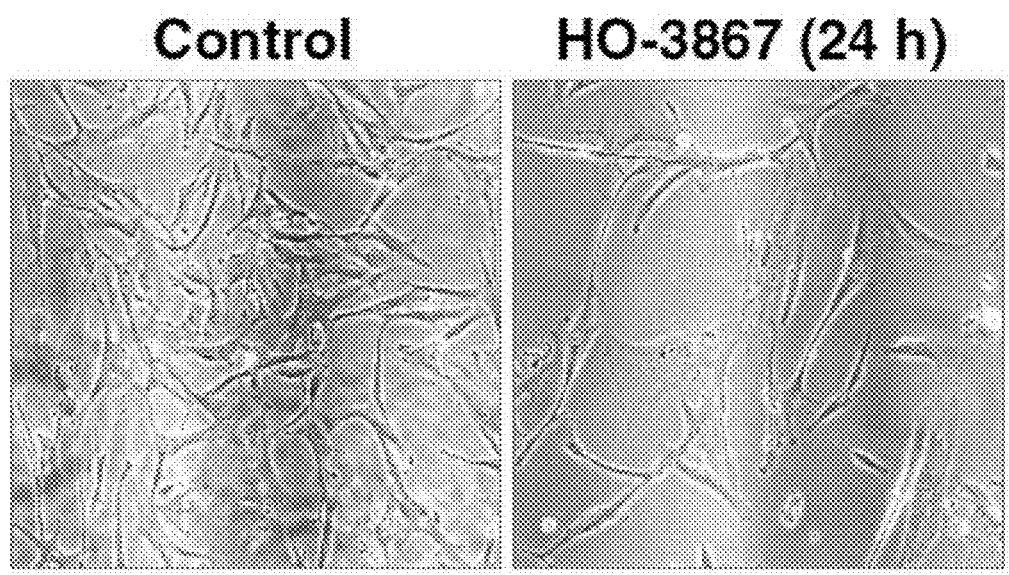
Figure 1C:
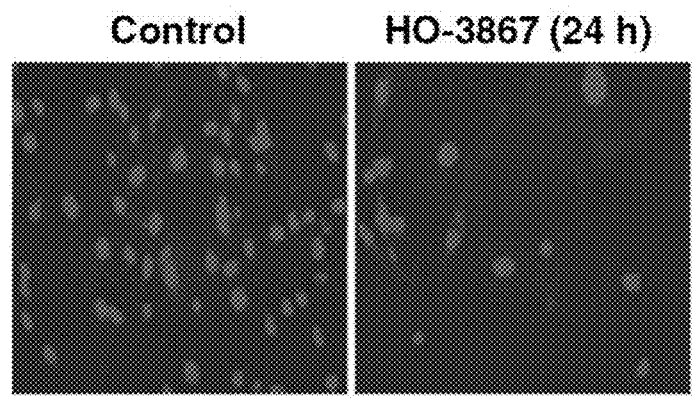
Figure 1D:
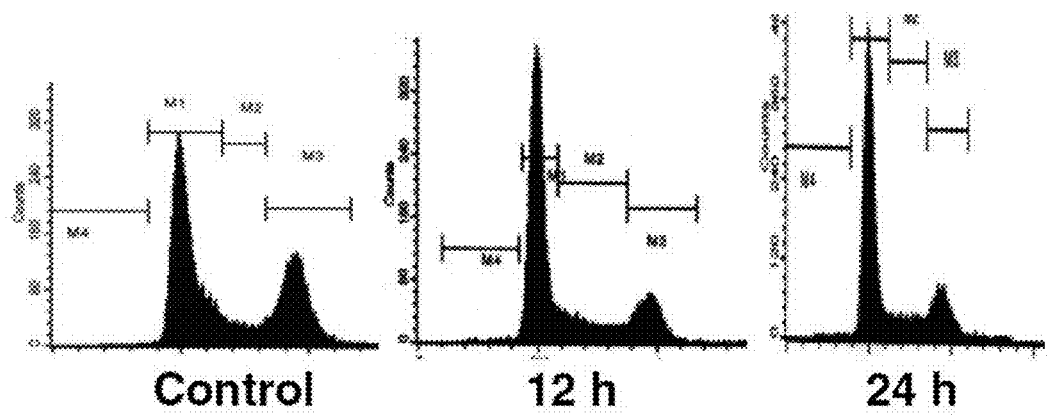
Figure 1E:
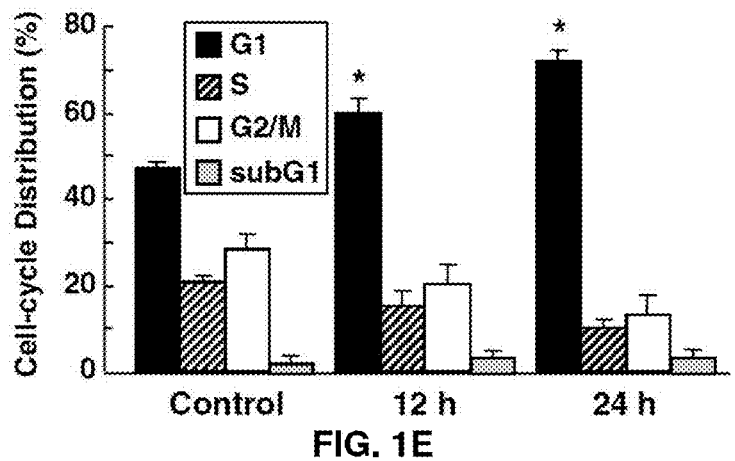

SMC proliferation was significantly increased upon treatment with 10% FBS for 24 h. The cells were then treated with 0, 0.5, 1, 5, and 10 μM HO-3867 for 24 h, after which the cells were trypsinized and counted for viability. The viable cell count decreased in a concentration-dependent manner after treatment with HO-3867. Significantly reduced cell-counts were observed at 1, 5, and 10 μM concentrations, the latter of which was used in all successive in vitro experiments. We determined the EC50 value to be 3.82 μM. We observed inhibition of SMC proliferation by both phase-contrast microscopy (FIG. 1B) and by nuclear staining with DAPI (FIG. 1C). Next, we determined whether the growth inhibition of SMC by HO-3867 was due to cell cycle arrest or apoptosis. SMCs were treated with 10 μM HO-3867 for 12 or 24 h. The cells were then fixed, and cell cycle populations were determined by flow cytometry. The results showed that HO-3867 induced G1 cell cycle arrest in SMCs in a time-dependent manner (FIG. 1D and FIG. 1E). There was no effect on the sub-$G_1$ population, indicating that HO-3867 did not induce apoptosis in SMCs at 12 or 24 h of treatment. The results show that HO-3867 inhibited the proliferation of human aortic SMCs through $G_1$ cell cycle arrest.

HO-3867 Induces Increased PTEN Expression and Activity in SMCs.

We investigated whether HO-3687 can increase the PTEN expression and/or activity in SMCs in vitro.

As shown in FIG. 2A, HO-3867 (10 μM) induced PTEN expression and PTEN activation (pPTEN) in cultured SMCs at as early as 1 h of treatment. This was further confirmed by immunofluorescence microscopy (FIG. 2B).

To confirm whether the increase in the expression of PTEN was due to its transcriptional induction by HO-3867, we performed RT-PCR analysis for PTEN mRNA. Cells treated with HO-3867 clearly showed an increase in PTEN mRNA expression in 3 h (FIG. 2C).

HO-3867 Activates ATF-2 in SMCs.

Western blot analysis showed that ATF-2 was activated by HO-3867 within 15 min (FIG. 3). We next wanted to check the involvement of reactive oxygen species-mediated p38 mitogen-activated protein kinase pathways in the activation of ATF-2. However, we did not detect the production of reactive oxygen species or activation of p38 mitogen-activated protein kinase in cultured SMCs (data not shown). These results how that HO-3867 directly activated ATF-2, thereby inducing PTEN expression in SMCs.

HO-3867-Induces $G_1$ Arrest, which is Partially Blocked by PTEN siRNA in SMCs.

To determine whether the HO-3867-induced growth inhibition in SMCs was attributable to PTEN, we treated PTEN siRNA-transfected SMCs with HO-3867 and analyzed cell cycle distribution by flow cytometry.

As shown in FIG. 4A, the level of PTEN, induced by HO-3867, was repressed in cells transfected with siRNA targeting PTEN compared with HO-3867-treated cells lacking PTEN siRNA or HO-3867-treated cells transfected with negative control siRNA. The suppression of PTEN using siRNA in HO-3867-treated cells resulted in an increase of pERK1/2 and decreased p53 and p21 levels. Cyclin D1 was not altered in the siRNA-treated group. In addition, suppression of PTEN increased cell survival (FIG. 4B) and partially blocked the HO-3867-induced cell cycle arrest (FIG. 4C) and apoptosis (FIG. 4D). These results show that PTEN plays a role in the G1 cell cycle arrest and apoptosis caused by HO-3867.

HO-3867 Down-Regulates MMP-2, MMP-9, NF-κB and FAK.

We investigated whether the HO-3867-induced PTEN expression could suppresses MMP expression in SMCs. The results (FIG. 5) revealed that HO-3867, through PTEN, down-regulated MMP-2 and MMP-9 expression in SMCs.

In addition, HO-3867 inhibited NF-κB p65, one of the main regulator mechanisms in the inflammatory activation of MMP-9 in SMCs (FIG. 5A).

We further observed that the expression of FAK, another known target of PTEN, was down-regulated by HO-3867. These results clearly show that HO-3867 inhibited SMC proliferation through PTEN-mediated down-regulation of MMP-2, MMP-9, NF-κB, and FAK expression.

Overexpression of PTEN by PTEN cDNA Enhances Apoptosis in SMCs.

We investigated whether the PTEN overexpression was responsible for the inhibition of cell survival and proliferation in SMCs. We used wild-type PTEN cDNA transfection into SMCs for these experiments. Twenty-four hours after transfection, the cells were treated with 10 μM HO-3867 for 12 h. Cells transfected with PTEN cDNA showed a significantly reduced survival compared with nontransfected cells (FIG. 6 A).

Transfected cells treated with HO-3867 exhibited an even more significant reduction in their survival compared with untreated or nontransfected cells. Overexpression of PTEN by PTEN cDNA significantly increased the $G_1$ cell cycle arrest (FIG. 6 B).

Furthermore, the combination of PTEN cDNA overexpression and HO-3867 treatment significantly increased the apoptotic population (sub-$G_1$) compared with PTEN cDNA- or HO-3867-alone-treated groups (FIG. 6 B).

The combination treatment also showed a greater effect on the up-regulation of PTEN and inhibition of MMP-2, NF-κB, FAK, and survival proteins at 12 h (FIG. 6 D).

These results also showed a substantial increase in the cleaved caspase-3 levels in the PTEN cDNA+HO-3867-treated cells at 12 h, compared with untreated or nontransfected cells (FIG. 6 D). The results established that PTEN overexpression is responsible for the inhibition of cell survival and proliferation in SMCs treated with HO-3867.

HO-3867 Inhibits Neointimal Formation after Balloon Injury in Rat Carotid Artery.

We further performed in vivo experiments to evaluate the efficacy of HO-3867 in inhibiting neointimal formation after balloon injury in a rat carotid artery model of restenosis, as described under Materials and Methods. A significant intimal thickening was observed in the carotid arteries at 14 days after infliction of balloon injury (FIG. 7A).

The thickening was significantly inhibited in rats receiving HO-3867 for 14 days. The intima/media ratio was significantly reduced in animals receiving HO-3867 (FIG. 7B).

We then determined whether the observed inhibitory effect of HO-3867 treatment on neointimal formation was associated with changes in the expression of regulatory proteins that we studied in the growth-stimulated SMCs in vitro.

We observed that the PTEN expression was depressed drastically in rat carotid artery tissue after balloon injury compared with uninjured controls (FIG. 7C).

Although treatment with 5 mg/kg HO-3867 restored PTEN to the control level, treatment with 10 mg/kg HO-3867 increased the PTEN level significantly above control level. Animals treated with 5 mg/kg did not show any significant inhibition of neointimal formation (data not shown). Western blot analysis of the tissues showed down-regulation of MMP-2, MMP-9, NF-κB p6 5, pERK1/2, pAkt, and cyclin D1 and up-regulation of p53 and cleaved caspase-3 (FIG. 7D).

The activation of cleaved caspase-3 in the 10-mg/kg HO-3867 dose shows that the treatment also induced apoptosis in vivo. We also confirmed the MMP-2 and MMP-9 activity using gelatin zymography. The MMP-2 and MMP-9 activities were significantly down-regulated in the treatment group compared with the injured/untreated group (FIG. 7E).

These results strongly show that HO-3867 inhibited neointimal formation by up-regulation of PTEN expression, leading to down-regulation of MMP-2, MMP-9, and NF-κB expressions in the rat carotid artery model of restenosis.

Discussion

This Example 1 demonstrates the application of a novel synthetic composition, HO-3867, for inhibition of SMC proliferation through up-regulation of PTEN expression.

The results showed pharmacologic inhibition of human aortic SMC proliferation in vitro and substantially reduced neointimal formation in vivo by HO-3867. The in vitro cell culture results showed that HO-3867 inhibited FBS-induced SMC proliferation through cell cycle arrest at the $G_1$ phase and by induction of apoptosis. This inhibitory effect was mediated by up-regulation of PTEN expression and several key growth-regulatory proteins including cyclin D1, MMPs, NF-κB, and ERK1/2. The in vitro studies using SMCs transfected with PTEN siRNA and PTEN cDNA confirmed that the HO-3867-induced overexpression of PTEN was responsible for the inhibition of SMC proliferation. The in vivo experiments in a rat carotid artery balloon injury model further showed a substantial depression of PTEN expression, which was restored far and beyond the control level after treatment with HO-3867.

HO-3867 specifically inhibits highly proliferating cells, such as stimulated SMCs or cancer cells, while sparing non-proliferating healthy cells. The EC50 value of HO-3867 in human SMCs was 3.82 μM.

A 10 μM concentration of HO-3867 was used to show its inhibitory effect on serum-stimulated SMCs. However, the same concentration of HO-3867 did not have any significant inhibitory effect on Chinese hamster ovary cells or human aortic endothelial cells, showing that the cytotoxic effect of HO-3867 is specific to proliferating cells.

The results of the present Example 1 show that HO-3867 increased PTEN expression in SMCs by activation of ATF-2 phosphorylation and its binding to the PTEN promoter.

The HO-3867-mediated activation of PTEN inhibited cell cycle progression by induction of p53 and p21 and down-regulation of ERK1/2 and cyclin D1, but without any change in Akt level.

Inhibition of MMP-2 and MMP-9 expressions in SMCs treated with HO-3867 (FIG. 5) was also shown herein. Also, overexpression of PTEN using wild-type PTEN cDNA also inhibited the expression of MMP-2 at an early stage of treatment (FIG. 6).

Furthermore, silencing of PTEN expression (using PTEN siRNA) had no effect on the HO-3867-induced inhibition of MMP-2 levels (data not shown), suggesting that the HO-386-induced inhibition of MMP-2 is a direct effect, independent of PTEN.

In fact, HO-3867 did not have any effect on MMP-2 in PTEN-overexpressing (transfected with PTEN cDNA) cells, beyond that of HO-3867 alone or PTEN cDNA treatments. However, the overexpression of PTEN, in combination with HO-3867, induced a significant level of apoptosis by activation of cleaved caspase-3 (FIG. 6 B).

Thus, Example 1 provides the first evidence that overexpression of PTEN, in combination with a synthetic composition, not only inhibits proliferation but also induces cell cycle arrest and apoptosis in SMCs. The siRNA studies clearly established a link between PTEN expression and induction of cell cycle arrest and apoptosis.

The rat carotid artery balloon injury model that we have used in this study is characterized by a high degree of reproducibility, with the development of SMC-rich intimal lesions. The relatively short treatment period (2 weeks) resulted in a significantly diminished neointima formation after balloon injury. The rapid action of HO-3867 in vivo show that the expressions of MMPs, ERK1/2, and NF-κB were more effectively suppressed in the tissue than in cultured cells. Thus, HO-3867 represents an attractive, potentially effective therapeutic agent for attenuating the vascular response to injury leading to restenosis.

The Example 1 shows that overexpression of PTEN by a synthetic composition effectively suppresses cell cycle progression in human SMCs and inhibits neointimal hyperplasia in a rat carotid artery injury model. These results show that PTEN can be a key target for the prevention of vascular proliferative disorders such as restenosis, and compositions such as HO-3867, which can up-regulate PTEN expression, can serve as useful therapeutic agents in this regard.

Example 2

Pharmaceutical Compositions

The active ingredient(s)s of the invention, and derivatives, fragments, analogs, homologs pharmaceutically acceptable salts or hydrate thereof, can be incorporated into pharmaceutical compositions suitable for administration, together with a pharmaceutically acceptable carrier or excipient. Such compositions typically comprise a therapeutically effective amount of any of the active ingredient(s)s described herein, and a pharmaceutically acceptable carrier. Preferably, the effective amount is an amount effective to selectively induce terminal differentiation of suitable neoplastic cells and less than an amount which causes toxicity in a subject.

Any inert excipient that is commonly used as a carrier or diluent may be used in the active ingredient(s)s of the present invention, such as for example, a gum, a starch, a sugar, a cellulosic material, an acrylate, or mixtures thereof. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release active ingredient(s).

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active ingredient(s), use thereof in the compositions is contemplated. Supplementary active ingredient(s) can also be incorporated into the compositions.

Non-limiting examples of solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

Non-limiting examples of liquid active ingredient(s), pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In certain embodiments, the active ingredient(s) can be prepared with carriers that will protect the active ingredient(s) against rapid elimination from the body, such as a controlled release active ingredient(s), including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such active ingredient(s) will be apparent to those skilled in the art. The materials can also be obtained commercially from Alza Corporation and Nova Pharmaceuticals, Inc. These can be prepared according to methods known to those skilled in the art.

It is especially advantageous to formulate compositions in dosage unit form for ease of administration and uniformity of dosage. Dosage unit form as used herein refers to physically discrete units suited as unitary dosages for the subject to be treated; each unit containing a predetermined quantity of active ingredient(s) calculated to produce the desired therapeutic effect in association with the required pharmaceutical carrier. The specification for the dosage unit forms of the invention are dictated by and directly dependent on the unique characteristics of the active ingredient(s) and the particular therapeutic effect to be achieved, and the limitations inherent in the art of compositioning such an active ingredient(s) for the treatment of individuals.

The pharmaceutical compositions can be included in a container, pack, or dispenser together with instructions for administration. For example, the active ingredient(s) may be administered intravenously on the first day of treatment, with oral administration on the second day and all consecutive days thereafter. The active ingredient(s)s of the present invention may be administered for the purpose of preventing disease progression or stabilizing tumor growth.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the active ingredient(s) administered to the subject is less than an amount that would cause toxicity in the subject. In the certain embodiments, the amount of the active ingredient(s) that is administered to the subject is less than the amount that causes a concentration of the active ingredient(s) in the subject to equal or exceed the toxic level of the active ingredient(s). The optimal amount of the active ingredient(s) that should be administered to the subject in the practice of the present invention will depend on the particular active ingredient(s) used and the type of cancer being treated.

The active ingredient(s) herein may also contain more than one active ingredient(s) (a second medicament), preferably those with complementary activities that do not adversely affect each other. The type and effective amounts of such medicaments depend, for example, on the amount and type of active ingredients present in the active ingredient(s), and clinical parameters of the subjects.

Kits

In a further aspect, there is provided herein a kit for use in treatment and prevention of a metabolic disorder, the kit comprising: i) individual dosage forms of a pharmaceutical composition according to the invention; and ii) instructions for administration of the pharmaceutical composition to a subject in need thereof.

In a further aspect, the invention provides a kit for use in treatment and prevention of a metabolic disorder, the kit comprising: i) individual dosage forms, and ii) instructions for administration of the dosage form to a subject in need thereof.

In Vitro Methods

The present invention also provides in-vitro methods for selectively inducing terminal differentiation, cell growth arrest and/or apoptosis of neoplastic cells thereby inhibiting proliferation of such cells, by contacting the cells with an effective amount of a composition containing ouabain, or a pharmaceutically acceptable salt or hydrate thereof.

Although the methods of the present invention can be practiced in vitro, it is contemplated that the preferred embodiment for the methods of selectively inducing terminal differentiation, cell growth arrest and/or apoptosis of neoplastic cells, and the like will comprise contacting the cells in vivo, i.e., by administering the compositions to a subject harboring neoplastic cells or tumor cells in need of treatment.

Treatments

The active ingredient(s) may be administered in any dose, provided it is effective to treat the patient. A physician having ordinary skill in the art can readily determine and prescribe the effective amount of the pharmaceutical composition required, depending on such factors as the particular active ingredient(s) employed, prior clinical experience, the patient's characteristics and clinical history, the type and severity of disease or disorder, other medicines being given, and any side effects predicted. For example, the physician could start with doses of an active ingredient(s), employed in the pharmaceutical composition at levels lower than that required in order to achieve the desired therapeutic effect and gradually increase the dosage until the desired effect is achieved. The effectiveness of a given dose or treatment regimen can be determined, for example, by assessing signs and symptoms and/or assessing inhibition of structural damage or of radiographic progression in the patient using the standard measures of efficacy.

The dose may be by weight or a fixed dose, preferably a fixed dose regardless of weight. An example of a weighted dose is 375 mg/m$^2$ weekly×4. As a general proposition, the effective amount of the antibody administered parenterally per dose will be in the range of about 20 mg to about 5000 mg, by one or more dosages, which can be translated to a dose by weight.

In an alternative aspect, one may administer a second medicament. The combined administration includes co-administration, using separate formulations or a single pharmaceutical formulation, and consecutive administration in either order, wherein preferably there is a time period while both (or all) active agents simultaneously exert their biological activities. The second medicament includes, for example, chemotherapeutic agents, immunosuppressive agents, antibodies, cytokine antagonists, integrin antagonist (e.g., antibody), corticosteroids, or any combination thereof.

Any of the compositions described above, including prodrugs and active compositions produced by the kit, can be combined with at least one pharmaceutically-acceptable carrier to produce a pharmaceutical composition. The pharmaceutical compositions can be prepared using techniques known in the art. The composition can be prepared by admixing the composition with a pharmaceutically-acceptable carrier. Many pharmaceutically-acceptable carriers are known to those skilled in the art. These most typically would be standard carriers for administration to humans, including solutions such as sterile water, saline, and buffered solutions at physiological pH, which may optionally contain certain pharmaceutically acceptable solvents such as ethanol or dimethylsulfoxide. Many pharmaceutically acceptable solid carriers are also well known to those of ordinary skill, such as for example many mono-, di-, and polysaccharides such as sucrose, lactose, starches, pectins, and the like, as well as semi-synthetic or synthetic polymer such as hydroxyalkyl celluloses, dextrans, polyacrylates, polyvinylpyrrolidones, and the like. The pharmaceutical carrier(s) must be "acceptable" in the sense of being compatible with the other ingredients of the composition and not overly deleterious to the recipient thereof.

The pharmaceutical compositions can include sterile aqueous or non-aqueous solutions, suspensions, and emulsions. Examples of aqueous or non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

The pharmaceutical compositions can, where appropriate, be conveniently presented in discrete unit dosage forms and can be prepared by any of the methods well known in the art of pharmacy. Such methods include the step of bringing into association the active composition with liquid carriers, solid matrices, semi-solid carriers, finely divided solid carriers or combination thereof, and then, if necessary, shaping the product into the desired delivery system.

Pharmaceutical compositions suitable for oral administration can be presented as discrete unit dosage forms such as hard or soft gelatin capsules, cachets or tablets each containing a predetermined amount of the active ingredient; as a powder or as granules; as a solution, a suspension or as an emulsion. The active ingredient can also be presented as a bolus, electuary or paste. Tablets and capsules for oral administration can contain conventional excipients such as binding agents, fillers, lubricants, disintegrants, or wetting agents. The tablets can be coated according to methods well known in the art, e.g., with enteric coatings.

Oral liquid preparations can be in the form of, for example, aqueous or oily suspensions, solutions, emulsions, syrups or elixirs, or can be presented as a dry product for constitution with water or other suitable vehicle before use. Such liquid preparations can contain conventional additives such as suspending agents, emulsifying agents, non-aqueous vehicles (which can include edible oils), or one or more preservative.

The compositions can also be formulated for parenteral administration (e.g., by injection, for example, bolus injection or continuous infusion) and can be presented in unit dose form in ampules, pre-filled syringes, small bolus infusion containers or in multi-does containers with an added preservative. The compositions can take such forms as suspensions, solutions, or emulsions in oily or aqueous vehicles, and can contain formulatory agents such as suspending, stabilizing and/or dispersing agents. Alternatively, the active ingredient can be in powder form, obtained by aseptic isolation of sterile solid or by lyophilization from solution, for constitution with a suitable vehicle, e.g., sterile, pyrogen-free water, before use.

Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the compositions can be adapted to provide sustained release of the active ingredient employed, e.g., by combination thereof with certain hydrophilic polymer matrices, e.g., comprising natural gels, synthetic polymer gels or mixtures thereof. The pharmaceutical compositions according to the invention can also contain other adjuvants such as flavorings, coloring, antimicrobial agents, or preservatives.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated by reference herein, and for convenience are provided in the following bibliography.

Citation of any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A composition comprising the compound DAP-F(p)-NOH, which has the structure:

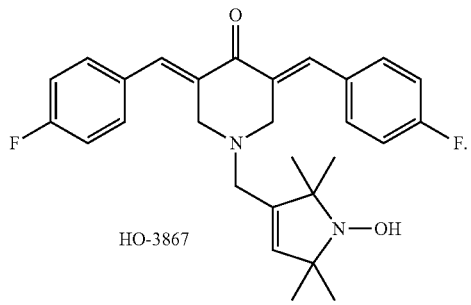 [SMILES: CC1(C)C=C(CN2C/C(=C\c3ccc(F)cc3)C(=O)/C(=C/c3ccc(F)cc3)C2)C(C)(C)N1O]

HO-3867

2. A composition useful for the treatment of post angioplasty restenosis, arteriosclerosis, and/or smooth muscle cell proliferation and/or neointimal hyperplasia in vascular tissues,
   comprising a composition of claim 1 and a pharmaceutically acceptable carrier.

3. A pharmaceutical composition for the treatment of human aortic smooth muscle cell (SMC) proliferation arrest in a subject in need thereof,
   comprising a composition of claim 1 and a pharmaceutically acceptable carrier.

4. A pharmaceutical composition for increasing phosphatase and tensin homolog (PTEN) expression and activity in SMCs in a subject in need thereof,
   comprising a composition of claim 1 and a pharmaceutically acceptable carrier.

5. A pharmaceutical composition for downregulating one or more of: matrix metalloproteinase-2 (MMP-2), MMP-9, nuclear factor kappa-light-chain-enhancer of activated B cells (NF-κB) and focal adhesion kinase (FAK) in a subject in need thereof,
   comprising a composition of claim 1 and a pharmaceutically acceptable carrier.

6. A pharmaceutical composition for inducing overexpression of PTEN by PTEN cDNA in order to enhance apoptosis in smooth muscle cells (SMCs) proliferation in a subject in need thereof,
   comprising a composition of claim 1 and a pharmaceutically acceptable carrier.

7. A pharmaceutical composition for inhibiting neointimal formation after injury in an artery in a subject in need thereof,
   comprising a composition of claim 1 and a pharmaceutically acceptable carrier.

8. A pharmaceutical composition for the treatment of post angioplasty restenosis, arteriosclerosis, and/or smooth muscle cell proliferation and/or neointimal hyperplasia in vascular tissues,
   comprising a composition of claim 1 and a pharmaceutically acceptable carrier.

\* \* \* \* \*